US006235308B1

(12) United States Patent
Barenholz et al.

(10) Patent No.: US 6,235,308 B1
(45) Date of Patent: May 22, 2001

(54) METHOD OF TREATING HYPERTENSION

(75) Inventors: Yechezkel Barenholz, Jerusalem; Hilary Shmeeda, Givat Zeez, both of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 08/257,866

(22) Filed: Jun. 10, 1994

(51) Int. Cl.$^7$ ........................ A61K 9/127; A61K 31/685
(52) U.S. Cl. ............................................. 424/450; 514/78
(58) Field of Search ................... 424/450; 514/78

(56) References Cited

U.S. PATENT DOCUMENTS

| | | | |
|---|---|---|---|
| 4,252,793 | 2/1981 | Altman | 424/199 |
| 4,308,166 | 12/1981 | Marchetti et al. | 252/316 |
| 4,310,505 | 1/1982 | Baldeschwieler et al. | 424/1 |
| 4,544,545 | 10/1985 | Ryan et al. | 424/1.1 |
| 4,812,314 | 3/1989 | Barenholz et al. | 424/450 |

FOREIGN PATENT DOCUMENTS

| | | |
|---|---|---|
| 0 050 793 | 5/1982 | (EP) . |
| 2 089 681 | 6/1982 | (GB) . |
| WO 86/00238 | 1/1986 | (WO) . |
| 86/01102 | 2/1986 | (WO) . |

OTHER PUBLICATIONS

Almog, S., et al., "States of aggregation and phase transformations in mixtures of phosphatidylcholine and octyl glucoside," Abstract only from *Biochemistry* 29 (*19*): 4582–2592 (1990).

Barenholz, Y., et al., "A Simple Method for the Preparation of Homogenous Phospholipid Vesicles," *Biochemistry* 16(*12*): 2806–2810 (1977).

Barenholz, Y., "Sphingomyelin–Lecithin Balance in Membranes: Composition, Structure, and Function Relationships," Chapter 5 from *Physiology of Membrane Fluidity, vol. 1* (Shinitzsky, M., ed., CRC Press, Inc., Florida, 1984, pp. 131–173).

Barenholz, Y., and T.E. Thompson, "Sphingomyelines in Bilayers and Biological Membranes," *Biochimica et Biophysica Acta 604*: 129–158 (1980).

Barenholz, Y., and S. Gatt, "Sphingomyelin: metabolism, chemical synthesis, chemical and physical properties," Chapter 4 from *Phospholipids* (Hawthorne, J.N., and G.B. Ansell, eds., Elsevier Biomedical Press, Amsterdam, 1982, pp. 129–177).

Barenholz, Y., et al., "A Calorimetric Study of the Thermotropic Behavior of Aqueous Dispersions of Natural and Synthetic Sphingomyelins," *Biochemistry* 15(*11*): 2441–2447 (1976).

Byers, S.O., and M. Friedman, "Transport of Cholesterol During Phosphatide–Induced Hypercholesterolemia," *Biochim. Biophys. Acta 125*: 157–165 (1966).

Byers, S.O., et al., "Mechanism Underlying Phosphatide–induced Hypercholesterolemia," The Journal of Biological Chemistry 237 (*11*) : 3375–3380 (1962).

(List continued on next page.)

*Primary Examiner*—Russell Travers
*Assistant Examiner*—S. Wang
(74) *Attorney, Agent, or Firm*—Foley & Lardner

(57) ABSTRACT

A method of treating hypertension and related symptoms thereof is described. A suspension of small, unilamellar vesicles composed primarily of phospholipids similar in nature to those of egg phosphatidylcholine is administered parenterally to a subject in need of such treatment repeatedly and over an extended period of time of at least several days, until a significant drop in blood pressure is observed.

5 Claims, 3 Drawing Sheets

OTHER PUBLICATIONS

Cooper, R.A., "Abnormalities of Cell–Membrane Fluidity in the Pathogenesis of Disease," The New England Journal of Medicine 297(7): 371–377 (1977).

Frank, A., et al., "Spontaneous Transfer of Sphingomyelin between Phospholipid Bilayers," Biochemistry 22: 5647–5651 (1983).

Gabizon, A., et al., "Liposomes as in Vivo Carriers of Adriamycin: Reduced Cardiac Uptake and Preserved Antitumor Activity in Mice," Cancer Research 42: 4734–4739 (1982).

Howard, A.N., et al., "Atherosclerosis Induced in Hypercholesterolaemic Baboons by Immunological Injury; and the Effects of Intravenous Polyunsaturated Phosphatidyl Choline," Atherosclerosis 14: 17–29 (1971).

Kirby, C.J., and G. Gregoriadis, "A Simple Procedure For Preparing Liposomes Capable of High Encapsulation Efficiency Under Mild Conditions," Chapter 2 from Physiology of Membrane Fluidity, vol. 1 (Shinitzky, M., ed., CRC Press, Inc., Florida, 1984, pp. 19–22).

Martin, F.J., and R.C. MacDonald, "Phospholipid Exchange between Bilayer Membrane Vesicles," Biochemistry 15(2): 321–327 (1976).

Moscona–Amir, E., et al., "Role of Lipids in Age–Related Changes in the Properties of Muscarinic Receptors in Cultured Rat Heart Myocytes," Biochemistry 25: 8118–8124 (1986).

Patelski, J., et al., "Modification of Enzyme Activities in Experimental Atherosclerosis in the Rabbitt," Atherosclerosis 12: 41–53 (1970).

Stafford, W.W., and C.E. Day, "Regression of Atherosclerosis Effected by Intravenous Phospholipid," Artery 1(2): 106–114 (1975).

Williams, K.J., et al., "Intravenously Administered Lecithin Liposomes: A Synthetic Antiatherogenic Lipid Particle," Perspectives in Biology and Medicine 27(3): 417–431 (1984).

Yechiel, E., and Y. Barenholz, "Relationships between Membrane Lipid Composition and Biological Properties of Rat Myocytes," The Journal of Biological Chemistry 260(16): 9123–9131 (1985).

Yechiel, E., et al., "Lateral Mobility and Organization of Phospholipids and Proteins in Rat Myocyte Membranes," The Journal of Biological Chemistry 260(16): 9132–9136 (1985).

CA 119: 173862m, Soloviev et al., 1993.*

Soloviev et al., "Phospholipid vesicles (liposomes) restore endothelium–dependent cholinergic relaxation in thoracic aorta from spontaneously hypertensive rats," J Hypertension, vol. 11(6), pp. 623–627 (1993).*

* cited by examiner

METHOD OF TREATING HYPERTENSION

FIELD OF THE INVENTION

The present invention relates to a method for treating hypertension.

REFERENCES

Barenholz, Y., et al., *Biochemistry*, 16:2806 (1977).

Barenholz, Y., et al., *Liposome Technology*, 1993 (Gregoriadis, G., ed), p524–607, CRC Press, Boca Raton, Fla.

Cesarone, C., et al., *Anal Biochem*, 100:188 (1979).

Harrison, T. R., editor-in-chief, *Harrison's Principles of Internal Medicine, Twelfth Ed.*, p 1001–1015, McGraw Hill, Inc., 1991.

Hertz, R., et al., *Chem Phys Lipid*, 15:138 (1975).

Kasten, F. H., *Tissue Culture: Methods and Applications,* Kruse, P., Patterson, M., eds., p 72–81, Academic Press, 1973.

Levida, M. *Handbook of Nutrition in the Aged* (R. R. Watson ed.), CRC Press, pp 89–109 (1985).

Lowry, O., et al., *J. Biol Chem.*, 193:265 (1951).

Monti, E., et al., *Biochim Biophys Acta*, 1124:80 (1992).

Shinitsky, M., et al., *J. Biol Chem*, 249:2652 (1974).

Szoka, F., et al., *Ann Rev Biophys Bioeng*, 9:467 (1980).

Yechiel, E., et al., *J. Biol Chem.*, 260:9132 (1985).

BACKGROUND OF THE INVENTION

Hypertension, which refers to elevated arterial pressure, is a widespread health problem in developed countries. Diagnosis of hypertension depends on measurement of blood pressure, which is typically reported as a ratio of systolic pressure (arterial pressure during contraction of the heart muscle) to diastolic pressure (residual arterial pressure during relaxation of the heart muscle), reported in units of mmHg. A normal diastolic blood pressure is between about 60–85 mmHg. Diastolic pressures above 85 mmHg are generally diagnostic of hypertension. By some estimates, the arterial blood pressure of fifteen percent of American adults is in a hypertension range that requires medical treatment.

A number of factors have been implicated in the development of hypertension. These include heredity and a number of environmental factors such as salt intake, obesity, occupation, family size, and crowding. Additional factors which may modify the course of hypertension include age, race, sex, stress, diet, smoking, serum cholesterol, and glucose intolerance.

The effects of hypertension are numerous, with the most severe being premature death, commonly caused by heart disease related to hypertension. Hypertension imposes an increased work load on the heart; related effects on the heart include angina pectoris, increased myocardial mass or hypertrophy (enlarged heart), and, late in the disease, evidence of ischemia or infarction.

Neurologic effects of hypertension are commonly divided into retinal and central nervous system changes. With respect to retinal impact, increasing severity of hypertension is associated with focal spasm as well as hemorrhages, exudates and papilledema, which often produce scotomata, blurred vision and even blindness. Central nervous system dysfunction may cause occipital headaches, dizziness, lightheadedness, vertigo, tinnitus and dimmed vision.

Drug therapy is a common approach to treatment of hypertension. In general, antihypertensive drugs belong to one of five classes of compounds: diuretics, antiadrenergic agents, vasodilators, calcium entry blockers, and angiotensin-converting enzyme (ACE) inhibitors (e.g., Harrison, Katzung). Each of the types of drugs, though generally effective in reducing hypertension, has side effects, such as potassium depletion, hyperglycemia, hypokalemia, depression, carbohydrate intolerance, tachycardia, and/or allergic skin rashes, and in more severe cases, vomiting, fever, diarrhea, angina, and cardiac failure.

SUMMARY OF THE INVENTION

The present invention is based on the discovery that treatment of human subjects with intravenously administered liposomes of the type described herein results in a significant lowering of blood pressure without apparent side effects. The treatment also leads to a reversal of myocardial hypertrophy, a common side effect of elevated arterial pressure.

In one aspect, the invention includes a method for treating hypertension in a subject having elevated blood pressure. The method includes intravenously administering to the subject a suspension of small unilamellar liposomes composed primarily of phosphatidylcholine phospholipids having phase transition temperatures in the range between about −10 and 37° C. Administration is repeated over a period of at least several days and in an amount effective to produce a significant reduction in blood pressure.

Preferably, the liposomes in the suspension have sizes ranging predominantly between 0.02 and 0.08 microns and are composed of egg phosphatidylcholine.

Preferably, the liposomal suspension is administered 1–3 times per week, at a dose of between about 0.05 and 1 µg lipid/kg body weight. Administration of the liposomes is continued until a drop in blood pressure of at least about 10% is observed.

The features and details of the invention will become more apparent and appreciated by one skilled in the art to which this invention pertains from the following detailed description of the invention.

DETAILED DESCRIPTION OF THE INVENTION

I. Preparation of Liposomes

Figure 1:
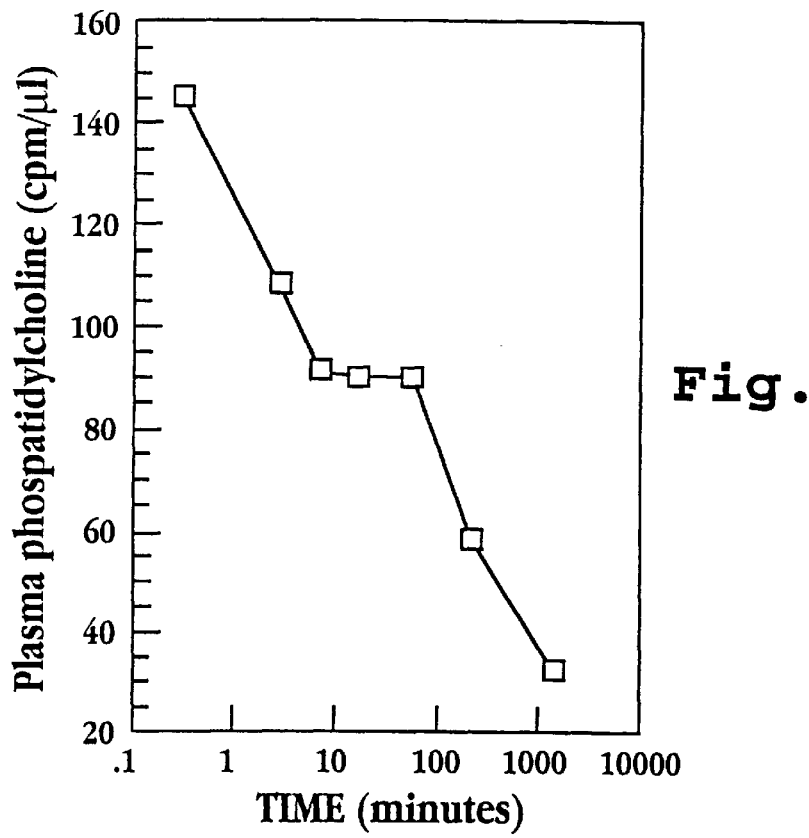
FIG. 1 illustrates the blood circulation time of intravenously administered PC SUV's in rat, measured as a function of plasma PC concentration over time.

The invention involves, in one aspect, administering a suspension of liposomes parenterally to an individual (a veterinary animal or human) to reduce hypertension. In one preferred embodiment, described and used in the examples below, the liposomes are composed predominantly (more than 50 mole percent, preferably more than 80–90 mole percent) of phosphatidylcholine (PC) having a phase transition temperature less than about 37° C., preferably between about −10 to 24° C., e.g., below about 5° C.

The liposome composition used in the method of the present invention is composed primarily of PC phospholipids. PC phospholipids include those phospholipids having a choline moiety and where the fatty acid chain portion of the phospholipid may vary in length and degree of unsaturation.

One preferred vesicle composition includes egg PC, which has a transition temperature of −5° C., and contains predominantly 1-palmitoyl, 2-oleyl PC and 1-palmitoyl,2-linoleyl PC. The liposomes may be composed entirely of the egg PC, or may contain other lipid components which (i) are not immunogenic, (ii) do not contribute a significant portion, i.e., more than 25–50 mole percent, of lipids with high phase transition temperature. Additional components may include negatively charged lipids, such as phosphatidylglycerol (PG) or phosphatidylserine (PS). Of course, the mole percentage of these lipids should be relatively low with respect to PC. The liposomes may also include cholesterol or other sterols, in an amount preferably less than about 40 mole percent.

Lipid protective agents, such as α-tocopherol, α-tocopherol acetate, or a-tocopherol succinate, may also be included in the lipids forming the liposomes, to protect the lipid components against free radical damage (Levida). Typically such agents are included at a mole percentage between about 0.5% and 2%. It is advantageous to add α-tocopherol to the liposomes to maintain a balance between vitamin E and polyunsaturated lipids in the liposomes.

A. Unsized Liposomes

A variety of methods for producing liposomes are available, and these have been extensively reviewed (Szoka 1980). In general these methods produce liposomes with heterogeneous sizes from about 0.02 to 10 microns or greater. As will be discussed below, liposomes which are relatively small and well defined in size are preferred for use in the present invention, hence a second processing step for reducing the size and size heterogeneity of liposomal suspensions will usually be required.

In one preferred method for forming the initial liposome suspension, the vesicle-forming lipids are taken up in a suitable organic solvent system, and dried in vacuo or under an inert gas to form a lipid film in a vessel. An aqueous suspension medium, such as a sterile saline solution, is added to the film, and the vessel is agitated until the lipids have hydrated to completion, typically within 1–2 hours. The amount of aqueous medium added is such as to produce a final liposome suspension containing preferably between about 10 and 30 g lipid per 100 ml media.

The lipids hydrate to form multilamellar vesicles (MLVs) whose sizes range between about 0.5 microns to about 10 microns or larger. In general, the size distribution of MLVs can be shifted toward slightly smaller sizes by hydrating the lipids under more vigorous shaking conditions. Example 1 describes the preparation of egg PC MLVs, prior to treating the MLVs with ultrasonic irradiation to reduce the liposome sizes.

The aqueous medium used in forming the liposomes may contain water-soluble agent(s) which enhance the stability of the liposomes upon storage. A preferred stabilizing agent is an iron-specific trihydroxamine chelating agent, such as desferrioxamine. The use of this compound in reducing lipid peroxidation and free radical damage in drug-containing liposomes has been reported in co-owned U.S. Pat. No. 4,797,285. Briefly, it was shown that the combination of a lipophilic free-radical quencher, such as α-tocopherol, and the water-soluble chelator gave substantially better protection against lipid peroxidation damage than did either protective agents alone. The chelator is included in the aqueous medium in molar excess of the amount of free iron in the medium. Typically, a chelator concentration of between about 10–200 micromolar is sufficient.

B. Sizing Liposomes

The suspension of liposomes prepared as above is preferably treated to produce a desired liposome size and size homogeneity.

The liposome suspension may be sized to achieve a selective size distribution of vesicles in a size range less than about 1 micron and preferably less than about 0.2–0.3 microns. Liposomes in this size range can be readily sterilized by filtration through a depth filter. Smaller vesicles also show less tendency to aggregate on storage, thus reducing potentially serious vascular blockage problems when the composition is administered parenterally. Finally, liposomes which have been sized down to the submicron range show more uniform biodistribution and drug clearance characteristics.

Figure 2:
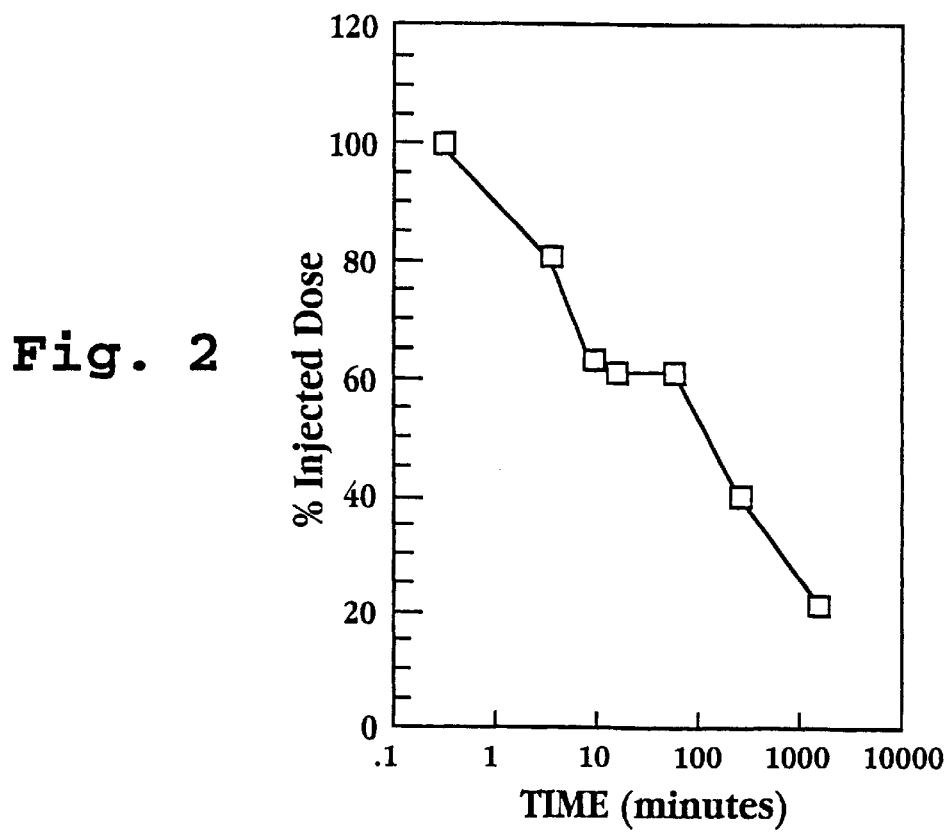
FIG. 2 illustrates the blood circulation time of intravenously administered PC SUV's in rat, measured as a function of percent injected dose over time.

Preferred liposomes are small unilamellar vesicles (SUVs), i.e., single-bilayer liposomes having sizes between about 0.02 to 0.08 microns. SUVs have relatively long blood circulation halflives, when administered intravenously. This is illustrated in FIGS. 1 and 2, which show plots of liposome retention in the bloodstream, measured up to 1,000 minutes after IV injection, and expressed either as PC measured in plasma (FIG. 1), or as percent injected dose (FIG. 2). As seen, significant amounts of liposomes remained in the bloodstream even at 1,000 minutes.

Several techniques are available for reducing the sizes and size heterogeneity of liposomes, in a manner suitable for the present invention. Ultrasonic irradiation of a liposome suspension either by bath or probe sonication produces a progressive size reduction down to SUVs. A sonicating procedure used to produce SUVs is described in Example 1. Homogenization is another method which relies on shearing energy to fragment large liposomes into smaller ones. In a typical homogenization procedure, MLVs are recirculated through a standard emulsion homogenizer until selected liposome sizes, typically less than 0.1 microns, are observed.

Extrusion of liposomes through a small-pore polycarbonate membrane is an effective method of reducing liposome size down to a relatively well-defined size distribution. An average range is between about 0.03 and 1 micron, depending on the pore size of the membrane, such as described in Example 2. Typically, the suspension is cycled through the membrane several times until the desired liposome size distribution is achieved. The liposomes may be extruded through successively smaller-pore membranes, to achieve a gradual reduction in liposome size.

The size-processed liposome suspension may be readily sterilized by passage through a sterilizing membrane having a particle discrimination size of about 0.2 microns, such as a conventional 0.22 micron depth membrane filter. If desired, the liposome suspension can be lyophilized for storage and reconstituted shortly before use.

II. Treatment Method and Results

In the treatment method of the invention, a liposomal suspension of the type described above is administered parenterally over an extended period of time of at least several days until a significant reduction in blood pressure is produced. The liposomal suspension is typically administered at a dosing frequency no greater than once per day, although dosing frequency may vary depending on the severity of the hypertensive condition, the age and overall general health of the subject, and other pre-existing conditions.

Additionally, and at any point in the treatment, the liposomal suspension may be administered in combination with other known antihypertensive agents to produce the desired reduction and or maintenance of blood pressure levels.

The liposomes may be conveniently administered as a series of dosages, given over a period of at least several days, and preferably maintained by continued doses at one to several month intervals over the lifetime of the treated individual. The amount of liposomes administered at each dose is between about 0.01 and 10 g lipid per kg of body weight, and preferably between about 0.05–1.0 g lipid per kg of body weight, although the dose may be substantially less. Long term dosages are typically delivered at a rate of between about 0.01–1 g lipid per kg body weight per day. In a preferred embodiment, the liposome suspension is administered 1–3 times per week, at a dose of between about 0.05 and 1 g lipid/kg body weight.

A typical dose for an 80 kg individual is between about 40 and 80 grams lipid, corresponding to between 200 and 400 ml of an up to 20 g lipid/100 ml suspension. Administration may be by iv (intravenous) bolus injection, but is preferably done by iv drip over a period of at least about 1 hour, to minimize tissue and blood trauma at the site of administration. The liposomes may be suspended in sterile saline or in a nutritional or drug-containing medium, such as a glucose/salt medium, to combine liposome treatment with other parenteral therapy.

Before the first dose is given, a minimum of two blood pressure measurements may be taken to provide a baseline for comparison over the course of liposome treatment. The liposome treatment is continued until a significant drop in both systolic and diastolic blood pressure of at least 5 percent is produced, and preferably, of at least about 10% or more.

Following the first liposome administration, blood pressure is measured, and a second liposome dose is given, typically between 2 and 7 days subsequent the first dose. Blood pressure is monitored in the conventional fashion in the upper arm with a sphygmomanometer. Values for both systolic and diastolic pressure are obtained and recorded. Further liposomal doses may likewise be given at 2–7 day intervals until either the blood pressure measurements begin to plateau or blood pressure measurements within the "normal" range are achieved. Thereafter, the subject may be maintained within the target blood pressure range by periodic maintenance liposome treatments, e.g., every 1–2 months.

A. Effect on Blood Pressure

In support of the invention, a suspension of SUV liposomes was administered to two human volunteers. As described in Example 3, blood pressure was measured over the treatment period of 16 days, during which seven liposomal treatments were administered. The results are shown in Table I and in FIGS. 3 and 4. As seen in Table I, blood pressure levels declined by approximately 20% from the Day 1 baseline value in both of the human subjects after the seventh treatment.

TABLE I

| | Blood Pressure, mmHg | | | | | | |
|---|---|---|---|---|---|---|---|
| Subject | 1st Treatment Day 1 | 2nd Day 3 | 3rd Day 7 | 4th Day 9 | 5th Day 11 | 6th Day 13 | 7th Day 16 |
| A | 125/75 | 115/75 | 115/65 | 110/60 | 100/60 | No Readings | 100/65 |
| B | 120/80 | 115/75 | 115/65 | 105/60 | 100/60 | | 100/60 |

Figure 3:
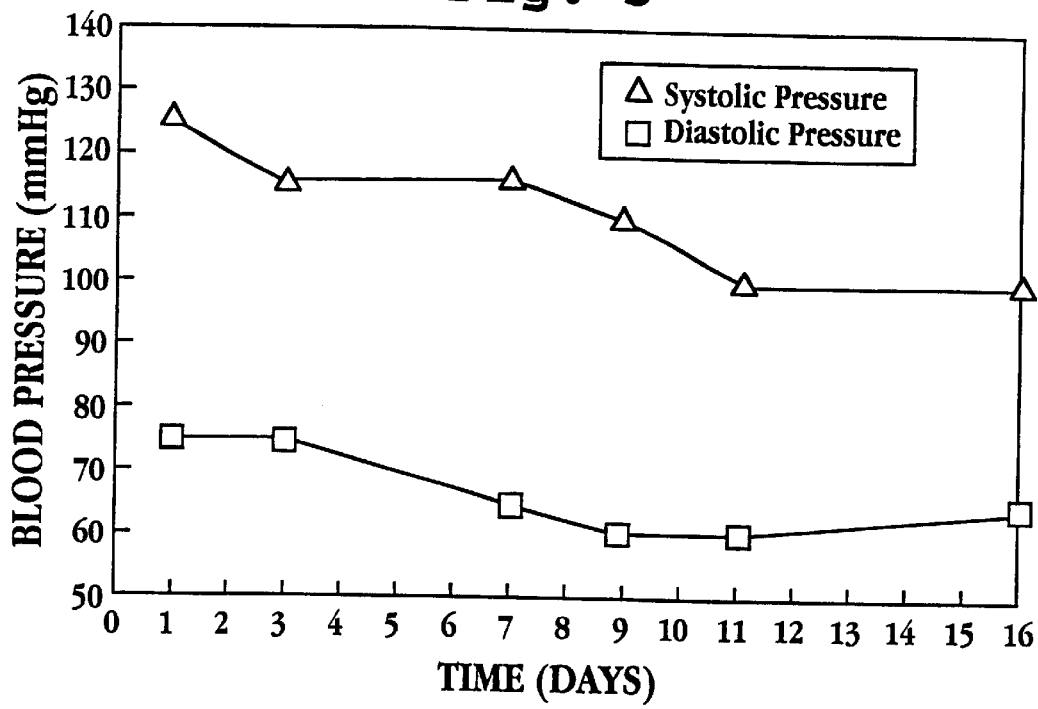
FIG. 3 is a graph of systolic (open triangles) and diastolic (open squares) blood pressure in one human volunteer as a function time after liposome treatment in accordance with the invention.
Figure 4:
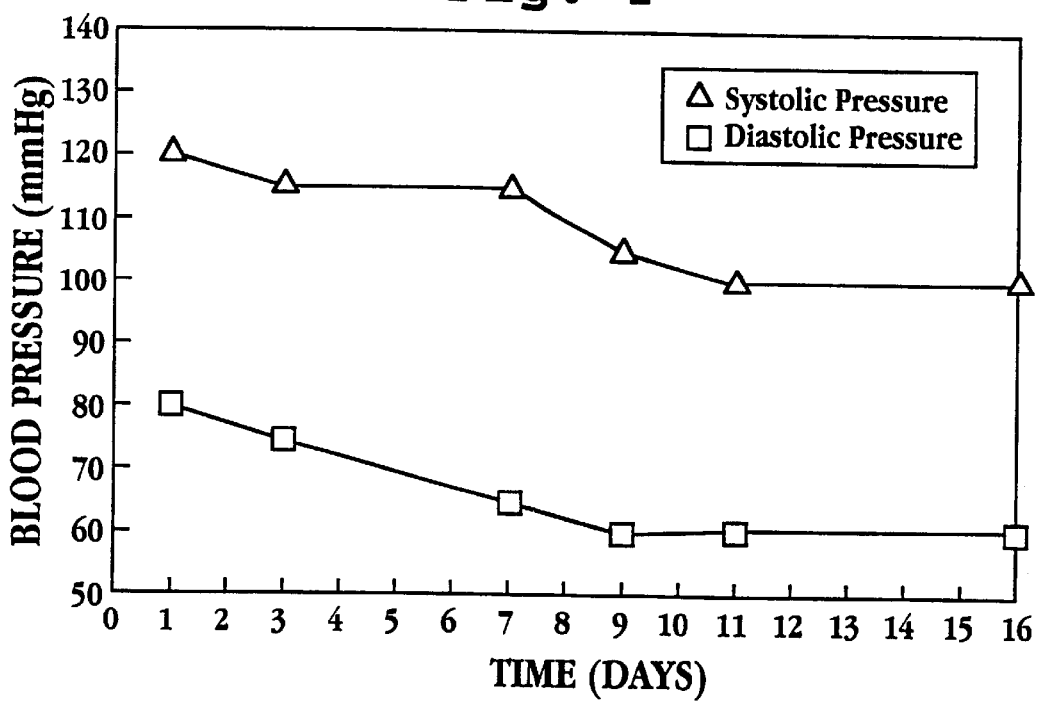
FIG. 4 is a plot similar to FIG. 3 for a second human volunteer.

The blood pressure data for volunteers A and B is plotted in FIGS. 3 and 4, respectively. The figures show that a reduction in both systolic pressure (open triangles) and diastolic pressure (open squares) occurs following treatment with the liposomal suspension, in accordance with the method of the invention.

B. Effect on Cardiac Hypertrophy

As discussed above, one side effect of hypertension is cardiac hypertrophy. Experiments were done to show that a reduction in cardiac hypertrophy is observed in hypertrophied cells treated according to the method of the invention.

As described in Example 4, the effect of egg PC liposome treatment on myocardial hypertrophy was determined by administering liposomes to laboratory rats ranging in age from 1.5 to 2 years. The animals were treated by iv (femoral vein) administration of SUVs every three days for six days with 0.5–1 g lipid per animal.

Three days after the final injection, the animals were sacrificed, and the heart mass, expressed as heart mass (wet mass) to total body mass of the animals, was determined for both the treated and the control animals, and the results shown in Table II below. The data in the table represent the average values for each group (treated versus untreated). As seen, the treatment method resulted in a marked reduction in heart mass.

TABLE II

| Group | Size, n | Heart mass (wet)/ Total body mass | Standard Deviation |
|---|---|---|---|
| treated | 6 | 0.0045 | 0.0003 |
| untreated | 5 | 0.0058 | 0.0004 |

C. Calcium Uptake

Experiments were carried out to investigate the effect of liposome treatment on hypertrophic myocyte cells, and in particular, on the levels of cellular calcium uptake. Calcium overload is known to be one of the more prominent features of the hypertrophic heart and is considered to be a critical factor in causing irreversible ischemic damage in hypertension. It was discovered that increased levels of calcium incorporated in older, hypertrophied cells were reversed upon treatment with egg PC SUVs, as reported in the study described in Example 5.

Figure 5:
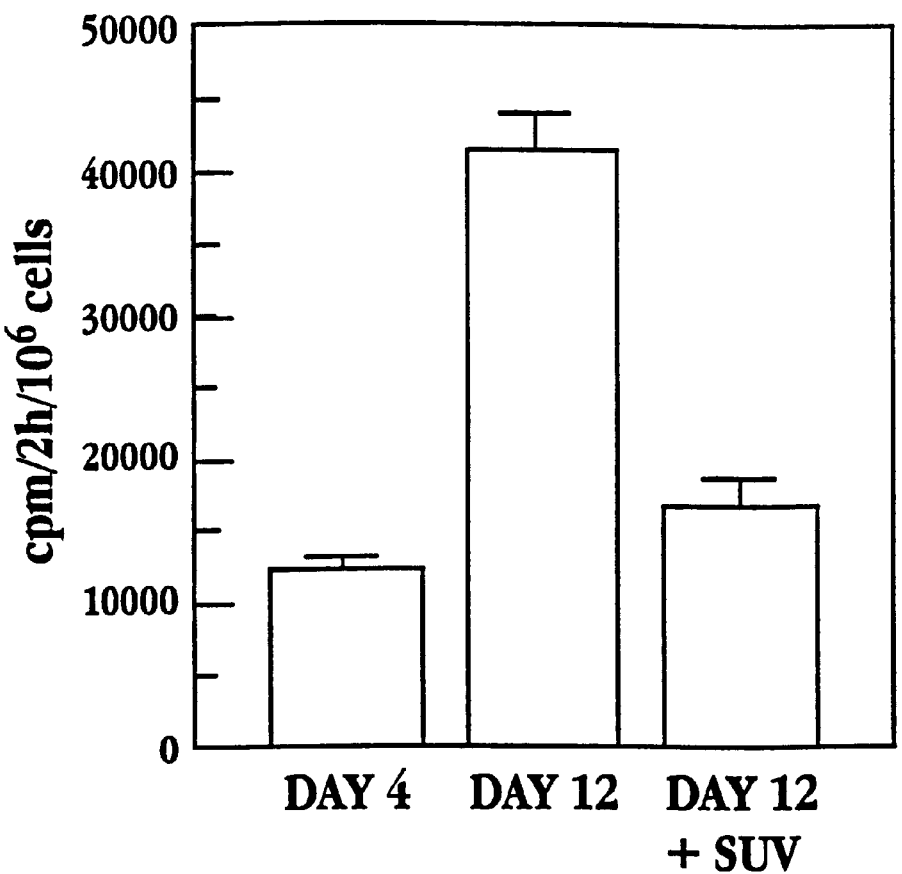
FIG. 5 is a bar graph showing uptake of $^{45}Ca^{2+}$ in myocyte cells that are 4 days old, 12 days old and 12 days old treated with PC SUV liposomes.

In this study (Example 5), cellular calcium uptake in hypertrophied and in non-hypertrophied cells was measured after incubation of the cells in $^{45}Ca^{2+}$ for up to 2 hours at 37° C. The results are shown in FIG. 5, and, as seen, the older, hypertrophic cells (12 days old) exhibited a 3-fold increase in the level of calcium uptake as compared to the younger, non-hypertrophic cells (4 days old). However, after a 72 hour treatment with egg PC SUVs, a greater than 50 percent decrease in cellular calcium uptake was detected in the older cells, as seen in the bar of FIG. 5 labeled "Day 12+SUV".

From the foregoing, it will be appreciated how various objects and features of the invention are met. Experiments in support of the invention demonstrate that the liposomal treatment method is effective to significantly reduce blood pressure after a relatively short treatment period, e.g., two weeks. The treatment method employs only natural phospholipids and is relatively safe.

It was also shown that the treatment is effective to reduce myocardial hypertrophy, one of the pathologies associated with elevated blood pressure.

The following examples illustrate methods of preparing liposome suspensions for use in the method, and various treatment methods. The examples are intended to illustrate, but in no way limit, the scope of the invention.

Materials

Egg phosphatidylcholine (egg PC) was prepared according to known methods (Shinitsky). High purity egg PC may also be purchased from Avanti Polar Lipids (Alabaster, AL) or Lipoid KG (Ludwigshafen, Germany). The egg PC was determined to be greater than 99% pure, based on thin layer chromatography (TLC) analysis. The egg PC fatty acid composition was similar to the reported composition (Hertz). The main PCs of the preparation included 1-palmitoyl,2-oleyl PC and 1-palmitoyl,2-linoleyl PC. Thin-layer chromatography plates, 0.25 silica gel HR and 0.024 silica gel, were obtained from Merck (Darmstadt, Germany) and Analtech (Newark, Del.), respectively.

EXAMPLE 1

Preparation of Small Unilamellar Vesicles: Sonication

Egg PC dissolved in chloroform was placed in a 100 ml vessel and dried to a thin film under nitrogen. Sterile saline was added to the lipid film to a final concentration of about 100 mg/ml, and the lipid film was hydrated with swirling. The resulting multilamellar vesicle (MLV) suspension was then bath sonicated for 1 hour using a Heat System Sonicator, Model 375W, at a power setting of 40–50% full value. The temperature of the suspension was maintained at about 4° C. under nitrogen during sonication. The sonicated suspension was separated from large vesicles by ultracentrifugation at 100,000 g for 1 hour (Barenholz, 1977). The suspension of SUVs, having a concentration of about 100 mg/ml, was filter sterilized.

EXAMPLE 2

Preparation of Small Unilamellar Vesicles: Extrusion

Homogeneous small unilamellar vesicles of egg PC with an average diameter of 39±8 nm, in 0.15 M NaCl were prepared by extrusion using serial filtration through polycarbonate filters in a GH 76-400 pressure cell (Nucleopore) (Amselem et al, 1993). Liposomal size was determined using a Coulter model N4 sub-micron particle analyzer equipped with a size distribution processor analyzer (Barenholz et al, 1993). The final extrusion step was through a 0.05 micrometer pore polycarbonate filter. Egg PC SUV's were sterilized by filtration through sterile 0.22 micrometer Millipore filters.

EXAMPLE 3

Effect of Egg PC SUV Treatment on Blood Pressure

To test the effect of egg PC liposome treatment on blood pressure, two volunteers were treated with egg PC SUV's made according to the procedures in Examples 1 or 2. The first human subject, herein designated as Volunteer A, was a 63 year old human male with a total body mass of 72 kg. The second subject, designated as Volunteer B, was a 29 year old human male with a body mass of 84 kg. Over a period of 16 days, seven liposome treatments, designated as Treatment 1, Treatment 2, etc., were administered intravenously to each subject. The dose of Treatments 1, 2 and 3 was 100 mg egg PC SUV per kg body weight. For Treatments 4, 5 and 6, a dose of 200 mg egg PC SUV/kg body weight was administered and Treatment 7 was dosed at 300 mg egg PC SUV per kg body weight.

The first liposome treatment, Treatment 1, was administered on day 1, and Treatments 2–7 were administered on days 3, 7, 9, 11, 13, and 16, respectively.

Blood pressure and pulse were monitored over the course of the study. Blood pressure measurements were taken in the artery of the upper arm and an initial measurement was taken in each subject prior to administration of the first liposome treatment, providing a baseline blood pressure for comparison with subsequent measurements.

The results of the study are shown in FIGS. 3 and 4 and in Table I. The blood pressure data corresponding to a given treatment represent an average of multiple blood pressure measurements taken over the 48 hour period following that treatment. As seen, Volunteer A (FIG. 3) exhibited a nearly 20% drop in both systolic and diastolic blood pressure; similarly, Volunteer B (FIG. 4) exhibited a nearly 20% drop in systolic pressure and a 25% drop in diastolic pressure.

EXAMPLE 4

Effect of Egg PC SUV Treatment on Myocardial Hypertrophy

Liposomes were administered to laboratory rats ranging from 1.5 to 2 years of age. The treated group contained 5 animals; the untreated group contained 6 animals. The animals were injected through the femoral vein with either sterile saline (untreated group) or with the SUV suspension of Example 1. The treated animals were injected every three days for six days with 0.5–1 g lipid per animal. The untreated animals received a similar volume of sterile saline over the same period. Three days after the final injection, the animals were sacrificed. The weight of each animal was determined. The heart was then removed, washed with cold saline and weighed. The ratios of heart mass (wet mass) to total body mass of the rats is given in Table II. The data in the table represent the average values for each group (treated versus untreated).

EXAMPLE 5

Effect of Liposome Treatment on Cellular Calcium Uptake in Hypertrophic Myocytes A. Preparation of Cell Cultures Myocyte cultures were prepared from the ventricular portion of one day old rat hearts (Sabra, Hebrew University-Hadassah Medical School). Fibroblasts were depleted by differential attachment for 60 minutes based on published procedures (Kasten, Yechiel). Myocytes were plated to reach a final density of approximately 10⁶ cells/35mm dish. Cultures were grown in Ham's F-10 media with the following supplements: sodium penicillin 200 U/l, streptomycin 200 mg/L, 20% fetal calf serum, and 0.1 mM 5-bromo-2-deoxyuridine. The combination of differential attachment, confluent plating of myocytes and the use of 5-bromo-2-deoxyuridine ensured less than 10% contamination with fibroblasts. Cultures were grown in 35 or 60 mm×15 mm Falcon culture dishes at 37° C. in 5% $CO_2$ for 14 days. The medium was changed every 48 h.

B. Characterization of Cells

The viability of 14 day cells was determined by trypan blue exclusion of trypsinized cells resuspended in 0.04% trypan blue for 15 min. Cells were then examined microscopically for uptake of the dye; trypan blue exclusion was greater than 95% in all samples of trypsinized cells. DNA was determined using calf thymus DNA as a standard (Cesarone). Determinations of DNA content and trypan blue exclusion in day 4 and day 14 cultures indicated that proper plating of cultures, i.e., those well dispersed before seeding and having greater than 90% confluency post-plating, ensured fluctuations of less than 10% in number. An additional indication of cell viability in older cultures was the full recovery of the beating rate (which had decreased by 70%) after treatment of cells at day 12 with egg PC liposomes.

Hypertrophy of cells was confirmed by measuring protein levels (Lowry) and protein synthesis based on [$^3$H]leucine incorporation in day 4 and day 14 cultures. Cells were incubated with 1 $\mu$Ci of [$^3$H]leucine (342 mCi/mmol) in leucine-free Ham's F-10 media supplemented with 1 $\mu$m leucine and 5% fetal calf serum for 24 h at 37° C. The cells were lysed in 0.1% SDS and protein was precipitated with ice-cold trichloroacetic acid (TCA) on Whatman GF/B glass filters. Filters were washed 3 times with 10% TCA and dried thoroughly before counting in 40% lumax in toluene. Cell size was quantitated by measuring the average surface area of cell monolayers labelled for 24 h with ceramide-lissamine-rhodamine in F-10 medium without phenol red and serum (Monti). Myocyte plasma membranes under these conditions were totally labelled after 24 h and the cell area was assessed using an ACAS 570 Interactive Laser Cytometer and Meridian computer image analysis program. An area of the culture dish was irradiated at room temperature (approximately 24° C.) using a 514 nm line argon laser operating at 100 mW power. For optimization of the spectral fit, a dichroic filter of 575 nm was used.

C. Effect of Liposomes

Cells (4 day old and 12 day old, hypertrophic) were incubated with 1 $\mu$Ci of $^{45}Ca^{2+}$ (2.32 mCi/mL) for up to 2 h at 37° C. in incubation media. Incorporation of labelled $Ca^{2+}$ was determined by the removal of the incubation media and the rapid addition of ice-cold media followed by four consecutive rapid washes in cold media. Non-specific binding was measured by the addition of 1 mM EGTA in the rapid washes and also by incubating the cells for 1 h at 4° C. to allow binding of $Ca^{2+}$ without allowing appreciable uptake. The level of calcium uptake was determined by subtracting the cell-associated $^{45}Ca^{2+}$ obtained by incubation at 4° C.

Calcium uptake results, shown below in Table III and in FIG. 5 above, represent the average of two different experiments, each performed in triplicate. As seen, a three-fold increase in the uptake of calcium was detected in the older (day 12) cells than in the younger cells (day 4). The higher incorporation of $^{45}Ca^{2+}$ in the older, hypertrophic cultures correlates with the characteristic calcium overload of the hypertrophic heart. Sterilized egg PC SUVs were added to the older cultures to give a final lipid concentration of 1.0 mM and the liposome treatment was extended for 72 h. The uptake of calcium was determined to be reduced by over 50% for the liposome-treated cells.

TABLE III

| Calcium Uptake, cpm/2n/10⁶ cells | | |
| --- | --- | --- |
| Day 4 | Day 12 | Day 12, PC SUV treated |
| 12,500 | 42,000 | 17,000 |

While various embodiments of the invention have been described herein, it will be apparent that various modifications can be made without departing from the scope of the invention.

It is claimed:

1. A method for treating hypertension in a subject having elevated blood pressure, comprising:

intravenously administering to the subject a suspension of small unilamellar liposomes composed primarily of phosphatidylcholine phospholipids having phase transition temperatures in the range between about −10 and 37° C., and repeating said administering over a period of at least several days and in an amount effective to produce a reduction in both systolic and diastolic blood pressure of at least 10 percent from said elevated blood pressure.

2. The method of claim 1, wherein the liposomes in the suspension have sizes between 0.02 and 0.08 microns.

3. The method of claim 1, wherein the liposomes in the suspension are composed of egg phosphatidylcholine.

4. The method of claim 1, wherein said liposome suspension is administered 1–3 times per week, at a dose of between about 0.05 and 1 g lipid/kg body weight.

5. The method of claim 1, wherein the phase transition temperature is less than about 5° C.

* * * * *